(12) United States Patent
Banowski et al.

(10) Patent No.: US 11,154,485 B2
(45) Date of Patent: Oct. 26, 2021

(54) CHITOSAN-CONTAINING ANTIPERSPIRANT COSMETIC AGENTS WHICH ARE FREE OF HALIDES AND/OR HYDROXY HALIDES OF ALUMINUM AND/OR ZIRCONIUM

(71) Applicant: Henkel AG & Co. KGaA, Duesseldorf (DE)

(72) Inventors: Bernhard Banowski, Duesseldorf (DE); Stefan Evers, Haan (DE); Marcus Claas, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/372,939

(22) Filed: Apr. 2, 2019

(65) Prior Publication Data

US 2019/0224102 A1 Jul. 25, 2019

Related U.S. Application Data

(63) Continuation of application No. 15/492,642, filed on Apr. 20, 2017, now abandoned, which is a continuation of application No. PCT/EP2015/072550, filed on Sep. 30, 2015.

(30) Foreign Application Priority Data

Oct. 24, 2014 (DE) .................... 10 2014 221 673.7

(51) Int. Cl.

| | |
|---|---|
| *A61K 8/73* | (2006.01) |
| *A61K 8/891* | (2006.01) |
| *A61K 8/06* | (2006.01) |
| *A61K 8/19* | (2006.01) |
| *A61K 8/34* | (2006.01) |
| *A61K 8/86* | (2006.01) |
| *A61K 8/36* | (2006.01) |
| *A61K 8/368* | (2006.01) |
| *A61K 8/37* | (2006.01) |
| *A61K 8/44* | (2006.01) |
| *A61K 8/58* | (2006.01) |
| *A61Q 15/00* | (2006.01) |

(52) U.S. Cl.

CPC ............. *A61K 8/736* (2013.01); *A61K 8/06* (2013.01); *A61K 8/19* (2013.01); *A61K 8/34* (2013.01); *A61K 8/342* (2013.01); *A61K 8/345* (2013.01); *A61K 8/36* (2013.01); *A61K 8/368* (2013.01); *A61K 8/37* (2013.01); *A61K 8/44* (2013.01); *A61K 8/585* (2013.01); *A61K 8/86* (2013.01); *A61K 8/891* (2013.01); *A61Q 15/00* (2013.01); *A61K 2800/26* (2013.01); *A61K 2800/30* (2013.01); *A61K 2800/882* (2013.01)

(58) Field of Classification Search

None
See application file for complete search history.

(56) References Cited

U.S. PATENT DOCUMENTS

2003/0133891 A1* 7/2003 Panzer ................. A61K 8/0241
424/65
2013/0280175 A1 10/2013 Banowski et al.

FOREIGN PATENT DOCUMENTS

| DE | 102010055816 A1 | 6/2012 |
| DE | 102012222692 A1 | 9/2013 |
| EP | 0803513 A1 | 10/1997 |
| WO | 9623479 A2 | 8/1996 |

OTHER PUBLICATIONS

Google patent search for chitosan deodorant_Feb. 26, 2020 (Year: 2020).*

Makin, S.A. et al. "Chapter 6: Deodorant Ingredients". "Antiperspirants and Deodorants, Second Edition, Revised and Expanded", edited by Karl Laden, Marcel Dekker Inc., 1999, pp. 183-184. ISBN: 08247-1746-5.

Hwang Kwon T. et al. "Controlling Molecular Weight and Degree of Deacetylation of Chitosan by Response Surface Methodology". Journal of Agricultural and Food Chemistry, vol. 50, No. 7, 2002, pp. 1876-1882.

PCT International Search Report PCT/EP2015/072550 completed: Dec. 16, 2015 dated Jan. 29, 2016 2 pages.

* cited by examiner

*Primary Examiner* — Michael P Cohen

(74) *Attorney, Agent, or Firm* — P. Scott Smith

(57) ABSTRACT

The invention relates to an antiperspirant cosmetic agent which includes at least one specific chitosan and which is free of aluminum-containing compounds, in particular free of halides and/or hydroxy halides of aluminum and/or zirconium. The present invention further relates to the use of a specific chitosan and to a non-therapeutic method for reducing body perspiration. Adding or using the at least one specific chitosan ensures that the sweat gland(s) is/are effectively influenced, thus resulting in a significant reduction in underarm perspiration even in the absence of antiperspirant aluminum-containing compounds.

10 Claims, No Drawings

CHITOSAN-CONTAINING ANTIPERSPIRANT COSMETIC AGENTS WHICH ARE FREE OF HALIDES AND/OR HYDROXY HALIDES OF ALUMINUM AND/OR ZIRCONIUM

FIELD OF THE INVENTION

The present invention generally relates to antiperspirant cosmetic agents that are free of aluminum salts and/or free of aluminum-zirconium salts and that include at least one substance selected from the group of cosmetic oils that are liquid at 20° C. and 1,013 hPa, odorous substances, and waxes, optionally at least one propellant, and at least one specific chitosan. The addition of the at least one specific chitosan results in an influence on the sweat gland(s).

Furthermore, the present invention relates to a packaging unit (kit of parts), including a cosmetic agent having at least one antiperspirant active substance (M1) and a cosmetic agent according to the invention (M2).

The present invention also relates to the use of specific chitosans to at least partially influence the sweat gland(s).

In addition, the present invention relates to the use of a combination, including at least one substance selected from the group of cosmetic oils that are liquid at 20° C. and 1,013 hPa, odorous substances, and waxes, optionally at least one propellant, and at least one specific chitosan, to reduce and/or prevent perspiration, particularly underarm perspiration or perspiration of other body regions. The combination according to the invention includes no aluminum-containing compounds.

Finally, the present invention relates to a non-therapeutic cosmetic method for preventing and/or reducing the perspiration of the body, wherein an antiperspirant cosmetic agent according to the invention or the agents (M1) and (M2) of the packaging unit according to the invention are applied to the skin, particularly to the skin of the axillae, and remain on the skin of the axillae for at least 1 hour, preferably for at least 2 hours, more preferably for at least 4 hours, particularly for at least 6 hours.

BACKGROUND OF THE INVENTION

The washing, cleaning, and care of one's own body is a basic human need, and modern industry is continually attempting to meet these human needs in a variety of ways. Especially important for daily hygiene is the lasting elimination or at least reduction of body odor and axillary moisture. Numerous specific deodorizing or antiperspirant body care agents developed for use in body regions having a high density of sweat glands, particularly in the axillary region, are known in the prior art. Said body care agents are formulated in a wide range of product forms, for example as a powder, stick, aerosol spray, pump spray, liquid and gel roll-on application, cream, gel, and impregnated flexible substrates (deodorant wipes).

Cosmetic antiperspirants of the prior art include, in addition to at least one oil or wax and one odorous substance component or perfume, at least one antiperspirant compound, particularly in the form of halides and/or hydroxy halides of aluminum and/or zirconium. Said antiperspirant compounds reduce the secretion of sweat of the body by temporarily constricting and/or plugging the excretory ducts of the sweat glands so that the amount of sweat can be reduced by approximately 20 to 60 percent. Furthermore, said antiperspirant compounds have an additional deodorizing effect because of the antimicrobial action of said antiperspirant compounds.

Halides and/or hydroxy halides of aluminum and/or zirconium, in conjunction with the acidic pH value of these antiperspirants, can lead to unpleasant skin reactions for some users. Furthermore, the use of the aforementioned antiperspirant compounds can lead to stains on clothing.

Therefore, there is a need for replacing antiperspirant halides and/or hydroxy halides of aluminum and/or zirconium with other antiperspirant cosmetic active substances. Said antiperspirant active substances should have good antiperspirant action and good skin compatibility and should be easy to formulate. Furthermore, said antiperspirant active substances should not have a negative effect on the storage stability of the antiperspirant cosmetic agents.

The present invention addresses the problem of providing an antiperspirant cosmetic agent that avoids or at least lessens the disadvantages of the prior art and that has good skin compatibility and also reliably reduces axillary moisture. Furthermore, the antiperspirant cosmetic agent should have high storage stability.

BRIEF SUMMARY OF THE INVENTION

Therefore, the subject of the present invention is an antiperspirant cosmetic agent, including
a) at least one substance selected from the group of cosmetic oils that are liquid at 20° C. and 1,013 hPa, odorous substances, and waxes,
b) propellant in a total amount of 0 to 99 wt %, with respect to the total weight of the antiperspirant cosmetic agent, and
c) at least one chitosan having a viscosity of 15 to 15,000 mPa*s, wherein the chitosan has the formula (I),

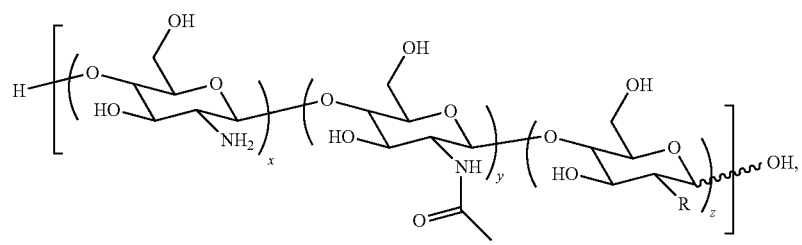

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units contained in the square brackets and having the indices x, y, and z can be freely chosen and the residue R is bonded by means of *, and d) no aluminum-containing compounds.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now surprisingly been found that the use of at least one specific chitosan in cosmetic agents without aluminum-containing compounds, particularly without antiperspirant halides and/or hydroxy halides of aluminum and/or zirconium, results in antiperspirant action that is nearly comparable to the antiperspirant action of formulations having aluminum salts and/or aluminum-zirconium complexes.

With no intention of being restricted to this theory, the use of the at least one chitosan in the antiperspirant cosmetic agents according to the invention results in a deliberate influence on the sweat gland(s). Said deliberate influence on the sweat gland(s) can consist, for example, in precipitation of the at least one chitosan at pH values that exist only within the excretory ducts of the sweat glands. In this way, effective plugging of the excretory ducts of the sweat glands can be ensured without a reduction in the antiperspirant action of the cosmetic agent according to the invention because of premature undesired precipitation due to the addition of the at least one specific protein. However, the deliberate influence on the sweat gland(s) can also consist in a disturbance of the charge equilibrium within the sweat gland(s), which leads to an effect on the production of sweat, particularly to a reduction in the production of sweat. Therefore, an effective reduction in underarm perspiration is ensured even in the absence of aluminum-containing compounds, particularly antiperspirant halides and/or hydroxy halides of aluminum and/or zirconium.

According to the invention, the term "antiperspirant" is understood to mean the reduction of the perspiration of the sweat glands of the body.

Furthermore, in the sense of the present invention, the term "cosmetic oil" is understood to mean an oil that is suitable for cosmetic use and that is not miscible with water in all amounts. The cosmetic oil used according to the invention is neither an odorous substance nor an essential oil.

In addition, in the sense of the present invention, the term "odorous substances" is understood to mean substances that have a molar mass of 74 to 300 g/mol, that include at least one osmophore in the molecule, and that have an odor and/or flavor, i.e., said substances are capable of stimulating the receptors of the hair cells of the olfactory system. Osmophores are groups, in the form of hydroxy groups, formyl groups, oxo groups, alkoxycarbonyl groups, nitrile groups, nitro groups, azide groups, etc., that are covalently bonded to the molecular skeleton. In this context, perfume oils, perfumes, or perfume oil constituents that are liquid at 20° C. and 1,013 hPa also fall under the term "odorous substances" in the sense of the present invention.

Furthermore, in the context of the present invention, the term "waxes" is understood to mean substances that are kneadable or solid to brittle and hard at 20° C., have a coarse to finely crystalline structure, and are colorfully translucent to opaque, but not vitreous. Furthermore, said substances melt above 25° C. without decomposition, flow readily (have low viscosity) slightly above the melting point, have a highly temperature-dependent consistency and solubility, and can be polished under light pressure.

Furthermore, according to the invention, the term "chitosans" is understood to mean deacetylation products of chitin that have a degree of deacetylation of more than 40% and that are soluble in 1% aqueous solutions of suitable acids, such as acetic acid, formic acid, citric acid, lactic acid, or hydrochloric acid. The viscosity of the chitosans used according to the invention is determined by means of a Brookfield RVDV II+, spindle no. 2, at 20 rpm and at 20° C., by using a 1 wt % solution of chitosan, with respect to the total weight of the solution, in 1% acetic acid.

Furthermore, in the context of the present invention, the term "aluminum-containing compounds" is understood to mean, in particular, chlorides, bromides, and iodides of aluminum and zirconium and compounds of the formulas $Al(OH)_yX$ and $Zr(OH)_zX$, wherein X represents a halide ion in the aforementioned formulas.

In addition, the term "fatty acids," as it is used in the context of the present invention, should be understood to mean aliphatic carboxylic acids that have unbranched or branched carbon residues having 4 to 40 carbon atoms. The fatty acids used in the context of the present invention can be naturally occurring fatty acids or synthetically produced fatty acids. Furthermore, the fatty acids can be mono- or polyunsaturated.

Finally, in the context of the present invention, the term "fatty alcohols" should be understood to mean aliphatic, monohydric, primary alcohols that have unbranched or branched hydrocarbon residues having 4 to 40 carbon atoms. The fatty alcohols used in the context of the invention can also be mono- or polyunsaturated.

In this document, the specification of wt % relates to the total weight of the propellant-free antiperspirant cosmetic agents according to the invention, unless otherwise indicated.

As a first constituent a), the cosmetic agents according to the invention include at least one substance selected from the group of cosmetic oils that are liquid at 20° C. and 1,013 hPa, odorous substances, and waxes.

In the context of the present invention, the cosmetic oil that is liquid at 20° C. and 1,013 hPa is selected from the group of (i) volatile cyclic silicone oils, particularly cyclic and linear silicone oils; (ii) volatile non-silicone oils, particularly liquid paraffin oils and isoparaffin oils; (iii) non-volatile silicone oils; (iv) non-volatile non-silicone oils; and (v) mixtures thereof.

According to the invention, the term "volatile oil" refers to oils that have a vapor pressure of 2.66 Pa to 40,000 Pa (0.02 to 300 mm Hg), preferably 10 to 12,000 Pa (0.1 to 90 mm Hg), more preferably 13 to 3,000 Pa (0.1 to 23 mm Hg), particularly 15 to 500 Pa (0.1 to 4 mm Hg), at 20° C. and an ambient pressure 1,013 hPa.

Furthermore, in the sense of the present invention, the term "non-volatile oils" is understood to mean oils that have a vapor pressure of less than 2.66 Pa (0.02 mm Hg) at 20° C. and an ambient pressure of 1,013 hPa.

According to the invention, it can be preferred that mixtures of volatile silicone oils and volatile non-silicone oils are used in the antiperspirant cosmetic agents according to the invention, because a drier skin feel is thereby achieved. Furthermore, it can be preferred in the context of the present invention if the antiperspirant cosmetic agents include a non-volatile silicone oil and/or a non-volatile non-silicone oil in order to mask insoluble constituents, such as talc or ingredients that are dried on the skin.

Especially preferred according to the invention is the use of mixtures of non-volatile and volatile cosmetic oils, because in this way parameters such as skin feel, visibility of the residue, and stability of the antiperspirant cosmetic agent according to the invention can be set and the agent can thus be better adapted to the needs of the consumers.

The volatile and non-volatile silicone oils and volatile and non-volatile non-silicone oils that can be used in the context of the present invention are disclosed, for example, in laid-open applications DE 102010063250 A1 and DE 10201222692 A1.

According to a preferred embodiment of the present invention, the cosmetic oil that is liquid at 20° C. and 1,013 hPa is included in a total amount of 0.02 to 98 wt %, preferably 2 to 85 wt %, more preferably 4 to 75 wt %, even more preferably 6 to 70 wt %, even more preferably 8 to 60 wt %, particularly 8 to 20 wt %, with respect to the total weight of the propellant-free antiperspirant cosmetic agent.

At least one odorous substance can also be included as constituent a) of the cosmetic agents according to the invention. However, mixtures of different odorous substances that together produce a pleasant scent are preferably used. Odorous substances that are usable in the context of the present invention are disclosed, for example, in laid-open application DE 102010063250 A1.

Especially pleasant-smelling antiperspirant cosmetic agents according to the invention are obtained if the at least one odorous substance is included in a total amount of 0.00001 to 15 wt %, preferably 0.001 to 9 wt %, more preferably 0.01 to 8 wt %, even more preferably 0.1 to 7 wt %, even more preferably 0.2 to 6 wt %, particularly 0.2 to 2 wt %, with respect to the total weight of the propellant-free antiperspirant cosmetic agent.

Furthermore, the antiperspirant cosmetic agents according to the invention can include a wax as constituent a). Said wax is preferably selected from the group of (i) fatty acid glycerol mono-, di-, and triesters; (ii) Butyrospermum Parkii (Shea Butter); (iii) esters of saturated, monohydric $C_{8-18}$ alcohols with saturated $C_{12-18}$ monocarboxylic acids; (iv) linear, primary $C_{12-24}$ alkanols; (v) esters of a saturated, monohydric $C_{16-60}$ alkanol and a saturated $C_{8-36}$ monocarboxylic acid; (vi) glycerol triesters of saturated linear $C_{12-30}$ carboxylic acids, which can be hydroxylated; (vii) natural plant waxes; (viii) animal waxes; (ix) synthetic waxes; and (x) mixtures thereof. Waxes that can be used with preference in the context of the present invention are disclosed in laid-open application DE 102012222692 A1.

In the context of the present invention, it is preferred if the wax is included in a total amount of 0.01 to 50 wt %, preferably 3 to 40 wt %, more preferably 5 to 30 wt %, particularly 6 to 25 wt %, with respect to the total weight of the propellant-free antiperspirant cosmetic agent.

According to one embodiment of the present invention, it can be provided that the antiperspirant cosmetic agents according to the invention include a propellant in a total amount of 0 to 99 wt %, with respect to the total weight of the propellant-free antiperspirant cosmetic agent, as constituent b). If the cosmetic agents according to the invention include a propellant, said propellant is preferably included in a total amount of 1 to 98 wt %, preferably 20 to 90 wt %, more preferably 30 to 85 wt %, particularly 40 to 75 wt %, with respect to the total weight of the antiperspirant cosmetic agent. In this case, the cosmetic agents according to the invention are formulated as propellant-gas-driven aerosols. Preferred propellants (propellant gases) are propane, propene, n-butane, isobutane, isobutylene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, and tetrafluoropropene, individually and in mixtures thereof. Hydrophilic propellant gases, such as carbon dioxide, can also be advantageously used according to the present invention if the proportion of hydrophilic gases is low and lipophilic propellant gas (e.g., propane/butane) is present in excess. Propane, n-butane, isobutane, and mixtures of these propellant gases are especially preferred. It has been found that the use of n-butane as a sole propellant gas can be especially preferred according to the invention.

The antiperspirant cosmetic agent according to the invention includes at least one specific chitosan according to formula (I) as a third constituent c).

Cosmetic agents according to the invention include at least one chitosan of formula (I) that has a viscosity of 15 to 15,000 mPa*s. The previously stated viscosity is preferably determined by means of a Brookfield RVDV II+, spindle no. 2, at 20 rpm and at 20° C., by using 1 wt % of chitosan of formula (I) in a 1 wt % acetic acid solution, with respect to the total weight of the solution. The solution is understood to be a 1 wt % acetic acid solution in which 1 wt % of the chitosan and 1 wt % of acetic acid, with respect to the total weight of said solution, are dissolved.

According to a preferred embodiment of the present invention, y represents integers from 1 to 22,000, preferably from 1 to 20,000, more preferably from 1 to 19,000, even more preferably from 1 to 18,000, particularly from 1 to 17,500, in formula (I).

Furthermore, it is preferred in the context of the present invention if x and z, independently of each other, represent integers from 5 to 20,000, preferably from 6 to 15,200, more preferably from 7 to 13,000, even more preferably from 8 to 12,500, particularly from 10 to 11,700, in formula (I). The use of chitosans of formula (I) having the previously stated numerical values for x, y, and z leads to an especially effective influence on the sweat gland(s) and therefore to an especially large reduction in perspiration.

In the context of the present invention, especially good results are obtained if chitosans of formula (I) that have a certain degree of deacetylation are used. Therefore, preferred antiperspirant cosmetic agents according to the invention are characterized in that the at least one chitosan of formula (I) has a degree of deacetylation of 70 to 99%, preferably 80 to 98%, more preferably 80 to 95%, even more preferably 80 to 92%, particularly 80 to 90%. The degree of deacetylation can be determined, for example, by means of NMR spectroscopy (Hwang, K. T. et al.; J. Agric. Food Chem.; 2002, 50, pages 1876 to 1882). Chitosans that have a degree of deacetylation of less than 70% have only insufficient solubility and therefore are not suitable for use in the antiperspirant agents according to the invention, because, as a result of the insolubility, the chitosan cannot enter the excretory ducts of the sweat gland(s) and therefore perspiration cannot be reduced.

The chitosan of formula (I) used in the antiperspirant cosmetic agents according to the invention can be obtained from various sources. However, it is preferred if the at least one chitosan of formula (I) is isolated from marine sources, particularly crabs, shrimps, krill, fungi, zooplankton, insects, microorganisms, modified microorganisms, or plant sources. The chitosan of formula (I) used in the antiperspirant cosmetic agents according to the invention is preferably obtained from marine sources, particularly from the chitin of crustaceans, which arise in large amounts in the preparation of crabs, lobsters, shrimps, etc. for food purposes. The chitin included there is typically deprotonated by the addition of bases, demineralized by the addition of mineral acids, and then deacetylated by using strong bases, such as concentrated sodium hydroxide solution. However, besides this production method, the chitosan of formula (I) can also be obtained from lower fungi such as *Absidia* sp., *Rhizopus* sp., and *Mucor* sp., which have chitosan as a cell wall component. Furthermore, it is also possible to obtain chitosan of formula (I) by using genetically modified microorganisms that synthesize chitosan by means of enzymatic processes. Chitosan can also be obtained from chitosan-containing plant sources.

In the context of the present invention, it is advantageous if the chitosans of formula (I) have a certain molecular weight. Therefore, preferred antiperspirant cosmetic agents according to the invention are characterized in that the at least one chitosan of formula (I) has an average molecular weight $M_w$ of 5,000 to 6,000,000 Da, preferably 6,000 to 5,500,000 Da, more preferably 8,000 to 5,050,000 Da, particularly 10,000 to 5,000,000 Da. The average molecular weight $M_w$ can be determined, for example, by gel permeation chromatography (GPC) (Hwang, K. T. et al.; J. Agric. Food Chem.; 2002, 50, pages 1876 to 1882). The use of chitosans having the previously stated molecular weights leads to an especially effective influence on the sweat gland(s) by precipitation of the chitosan within the sweat gland(s) or by disturbance of the charge equilibrium within the sweat gland(s) and therefore to excellent antiperspirant action of the cosmetic agents according to the invention.

According to the invention, chitosans of formula (I) that have a certain viscosity are especially preferably used. Therefore, it is preferred in the context of the present invention if the at least one chitosan of formula (I) has a viscosity of 15 to 10,000 mPa*s, preferably 15 to 8,000 mPa*s, more preferably 15 to 6,000 mPa*s, particularly 15 to 5,000 mPa*s, wherein the viscosity is determined by means of a Brookfield RVDV II+, spindle no. 2, at 20 rpm and at 20° C., and wherein 1 wt % of chitosan of formula (I) in a 1 wt % acetic acid solution, with respect to the total weight of the solution, is used to determine the viscosity. Chitosans that have a viscosity below 15 mPa*s do not result in the desired influence on the sweat gland(s). In contrast, chitosans having a viscosity of more than 15,000 mPa*s lead to formulation problems and usage problems of the cosmetic agents according to the invention because of the high viscosity and therefore are also not suitable in the context of the present invention.

In the context of the present invention, an especially effective reduction in underarm perspiration by means of the at least one chitosan of formula (I) is achieved if the at least one chitosan of formula (I) is included in a total amount of 0.05 to 40 wt %, preferably 0.1 to 35 wt %, more preferably 0.2 to 30 wt %, even more preferably 0.4 to 25 wt %, particularly 0.5 to 20 wt %, with respect to the total weight of the propellant-free antiperspirant cosmetic agent. With no intention of being restricted to this theory, the use of the aforementioned amounts of the at least one specific chitosan results in a significant influence on the sweat gland(s) by precipitation of the chitosan in the excretory ducts of the sweat glands or by an effect on the charge equilibrium within the sweat gland(s). In this way, excellent antiperspirant action is ensured. Furthermore, the use of the aforementioned amounts of the at least one specific chitosan does not lead to unstable formulations, and therefore the stability of the antiperspirant cosmetic agents according to the invention is ensured even over long time periods of storage.

According to another preferred embodiment of the present invention, the antiperspirant cosmetic agent has a pH value of pH 2 to pH 10. Within this range, a stable formulation of the cosmetic agents according to the invention is possible without the occurrence of undesired interactions between the ingredients. According to the invention, the desired pH value can be set by using acids and bases that are known to a person skilled in the art and that are common in antiperspirant cosmetic agents.

According to the invention, it is also preferred if the antiperspirant cosmetic agent additionally includes at least one preservative agent. Preservative agents preferred according to the invention are iodopropynyl butylcarbamate formaldehyde releaser, parabens, phenoxyethanol, ethanol, benzoic acid and salts thereof, dibromodicyanobutane, 2-bromo-2-nitropropane-1,3-diol, imidazolidinyl urea, 5-chloro-2-methyl-4-isothiazolin-3-one, 2-chloroacetamide, benzalkonium chloride, benzyl alcohol, salicylic acid, and salicylates. Other preservative agents that are usable in the context of the present invention are the substances listed in Annex 6 of the Cosmetics Regulation and cosmetic raw materials having preservative properties or raw materials that support or intensify the preservative action of the aforementioned preservative agents. The preservative agents are preferably included in a total amount of 0.01 to 10 wt %, preferably 0.1 to 7 wt %, more preferably 0.2 to 5 wt %, particularly 0.3 to 2.0 wt %, with respect to the total weight of the propellant-free antiperspirant cosmetic agent.

In the context of the present invention, it is preferred if the antiperspirant cosmetic agent exists in the form of a water-in-oil emulsion. In particular, the water-in-oil emulsion can be a sprayable water-in-oil emulsion, which can be sprayed by means of a propellant, or a gel-type water-in-oil emulsion, which can be applied by means of a dispenser. In this context, it is preferred if the antiperspirant cosmetic agent according to the invention existing in the form of a water-in-oil emulsion includes the at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %, with respect to the total weight of the propellant-free antiperspirant cosmetic agent.

However, it can be equally preferred according to the invention if the antiperspirant cosmetic agent exists as an oil-in-water emulsion. In this case, the cosmetic agent according to the invention is preferably sprayed as a propellant-containing aerosol or a propellant-free pump spray or squeeze spray or applied as a roll-on. In this context, it is preferred if the antiperspirant cosmetic agent existing in the form of an oil-in-water emulsion includes the at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %.

According to another preferred embodiment of the present invention, the cosmetic agents according to the invention can include only a small content of free water or no free water. In the sense of the present invention, the term "free water" is understood to mean water that is different from water of crystallization, hydration water, or similarly molecularly bound water of the constituents that are used. The antiperspirant cosmetic agent preferably includes free water in a total amount of less than 10 wt %, preferably less than 8 wt %, more preferably less than 5 wt %, even more preferably less than 3 wt %, even more preferably less than 1 wt %, particularly 0 wt %, with respect to the total weight of the propellant-free antiperspirant cosmetic agent.

However, in the context of another embodiment, it is also preferred according to the invention if the antiperspirant cosmetic agent exists as an aqueous, aqueous-alcoholic, or aqueous-glycolic solution. According to the invention, because the cosmetic agents according to the invention include no antiperspirant halides and/or hydroxy halides of aluminum and/or zirconium, which have reduced antiperspirant action as a result of the addition of protic solvents, protic solvents such as aqueous solutions can be used to formulate the antiperspirant cosmetic agents according to the invention without the occurrence of a significant reduction in the antiperspirant action. Therefore, the addition of the at least one specific chitosan ensures an effective influence on the sweat gland(s) and thus excellent antiperspirant action even if protic solvents are used.

In the context of this embodiment of the present invention, it was surprisingly found that the influence on the sweat gland(s) by the at least one specific chitosan of formula (I) can be significantly increased if the antiperspirant cosmetic agents according to the invention include free water in an amount of 5 to 99 wt %, with respect to the total weight of the propellant-free antiperspirant cosmetic agent. Therefore, in an especially preferred embodiment of the present invention, the antiperspirant cosmetic agent includes free water in a total amount of 5 to 96 wt %, preferably 15 to 80 wt %, more preferably 30 to 70 wt %, particularly 40 to 60 wt %, with respect to the total weight of the propellant-free antiperspirant cosmetic agent.

Furthermore, in the context of this embodiment, it is preferred if the antiperspirant cosmetic agent includes ethanol in a total amount of 1 to 99 wt %, preferably 5 to 70 wt %, more preferably 7 to 50 wt %, particularly 10 to 30 wt %, with respect to the total weight of the propellant-free antiperspirant cosmetic agent. As previously stated, because of the use of the at least one specific chitosan of formula (I), even large amounts of protic solvents such as ethanol can be used without the antiperspirant action of the antiperspirant cosmetic agent according to the invention being negatively affected.

The antiperspirant cosmetic agent according to the invention can be applied by means of various methods. According to a preferred embodiment, the antiperspirant cosmetic agent is formulated as a spray application. The spray application is accomplished by means of a spraying device, which includes a filling of the antiperspirant cosmetic agent according to the invention, which is liquid, viscously flowable, in the form of a suspension, or in the form of a powder, in a container. The filling can be under the pressure of a propellant (compressed-gas cans, compressed-gas packages, aerosol packages), or a mechanically operated pump atomizer without propellant gas (pump sprays/squeeze bottle) can be used. The antiperspirant cosmetic agent can be atomized physically, mechanically, or electromechanically, for example by means of piezoelectric effects or electric pumps. Containers and removal devices that are usable in the context of this embodiment are described, for example, in laid-open application DE 102012222692 A1.

Furthermore, the antiperspirant cosmetic agent can preferably be formulated as a stick, soft solid, cream, gel, roll-on, or loose or compact powder. The formulation of the antiperspirant cosmetic agents according to the invention in a certain product form, such as an antiperspirant roll-on, an antiperspirant stick, or an antiperspirant gel, is preferably based on the requirements of the intended use. Therefore, depending on the intended use, the antiperspirant cosmetic agents according to the invention can exist in solid, semi-solid, liquid, disperse, emulsified, suspended, gel, multi-phase, or powdery form. In the sense of the present invention, all types of solid dispersions in liquids also fall under the term "liquid". Furthermore, in the sense of the present invention, agents that have at least two different phases having a phase separation and in the case of which the phases can be arranged horizontal, i.e., one over the other, or vertical, i.e., one next to the other, are understood by multi-phase antiperspirant cosmetic agents according to the invention. The application can be performed, for example, by means of a roller-ball applicator or by means of a solid stick.

In the context of the present invention, it can also be preferred if the antiperspirant cosmetic agent is included on and/or in a disposable substrate, selected from the group of wipes, pads, and puffs. Especially preferred are wet wipes, i.e., preferably individually packaged wet wipes prefabricated for the user, which are well known, for example, from the field of glass cleaning or from the field of wet toilet wipes. Such wet wipes, which can advantageously also include preservative substances, are impregnated or loaded with an antiperspirant cosmetic agent according to the invention and are preferably packaged individually. Preferred substrate materials are selected from porous flat wipes. These wipes include wipes composed of woven and nonwoven synthetic and natural fibers, felt, paper, or foam, such as hydrophilic polyurethane foam. Deodorizing or antiperspirant substrates preferred according to the invention can be obtained by soaking or impregnation or by applying an antiperspirant cosmetic agent according to the invention to a substrate in melted form.

Besides the previously mentioned compounds, the antiperspirant cosmetic agent according to the invention can include further active substances and ingredients.

According to the invention, it is therefore preferred that the antiperspirant cosmetic agent includes at least one further auxiliary substance, selected from the group of (i) emulsifiers and/or surfactants; (ii) thickeners; (iii) chelating agents; (iv) deodorant active substances; (v) mono- and/or polyhydric alcohols and/or polyethylene glycols; (vi) skin-cooling active substances; (vii) pH adjusters; (viii) skin care active substances, such as moisturizers, skin-soothing substances, skin-lightening substances, skin-smoothing substances; and (ix) mixtures thereof.

Suitable emulsifiers and surfactants preferred according to the invention are selected from anionic, cationic, nonionic, amphoteric, particularly ampholytic and zwitterionic emulsifiers and surfactants. Surfactants are amphiphilic (bi-functional) compounds that consist of at least one hydrophobic molecule part and at least one hydrophilic molecule part. The hydrophobic residue is preferably a hydrocarbon chain having 8 to 28 carbon atoms, which hydrocarbon chain can be saturated or unsaturated, linear or branched. This $C_8$-$C_{28}$ alkyl chain is especially preferably linear. Emulsifiers and surfactants that are usable with preference in the context of the present invention are disclosed, for example, in laid-open applications DE 102012222692 A1, DE 102010063250 A1, and DE 102010055816 A1.

To thicken the antiperspirant cosmetic agents according to the invention, preferably substances selected from the following are used: cellulose ethers, xanthan gum, sclerotium gum, succinoglucans, polygalactomannans, pectins, agar, carrageenan, tragacanth, gum arabic, gum karaya, tara gum, gellan gum, gelatin, propylene glycol alginate, alginic acids and salts thereof, polyvinylpyrrolidones, polyvinyl alcohols, polyacrylamides, starches that are physically modified (e.g., by means of pre-gelatinization) and/or chemically modified, acrylic acid/acrylate copolymers, acrylic acid/acrylamide copolymers, acrylic acid/vinylpyrrolidone copolymers, acrylic acid/vinylformamide copolymers, and polyacrylates. Furthermore, especially preferred thickeners are selected from carbomers. Carbomers are thickening cross-linked polymers of acrylic acid, methacrylic acid, and salts thereof. The cross-linking can be accomplished by means of polyfunctional compounds such as polyalkylene ethers of polysaccharides or of polyalcohols, such as sucrose allyl ethers, pentaerythritol allyl ethers, propylene allyl ethers. Homopolymers of acrylic acid or salts thereof that are cross-linked by means of a pentaerythritol allyl ether, a sucrose allyl ether, or a propylene allyl ether are preferred in the context of the present invention. A copolymer of $C_{10-30}$ alkyl acrylate, acrylic acid, methacrylic acid, and esters thereof that is cross-linked by means of a sucrose allyl ether or a pentaerythritol allyl ether is a thickener that is usable in the context of the present invention. The products available under the trade name Carbopol® (BF Goodrich, Ohio, USA), such as Carbopol 934, Carbopol 940, Carbopol 941, Carbopol 971, Carbopol 974, Carbopol EZ2, Carbopol ETD 2001, Carbopol ETD 2020, Carbopol ETD 2050, Carbopol ultrez 10, Carbopol ultrez 20, or Carbopol ultrez 21, are thickeners based on carbomers.

Furthermore, lipophilic thickeners can be used to thicken the antiperspirant cosmetic agents according to the invention. Lipophilic thickeners preferred according to the invention are selected from hydrophobed clay minerals, bentonites, pyrogenic silicic acids, and derivatives thereof.

To further support the influence of the at least one specific chitosan of formula (I) on the sweat gland(s), it can be advantageous to add at least one chelating agent to the antiperspirant cosmetic agents according to the invention in a total amount of 0.01 to 3.0 wt %, preferably 0.02 to 1.0 wt %, particularly 0.05 to 0.1 wt %, with respect to the total weight of the propellant-free antiperspirant agent according to the invention. In the context of the present invention, preferred chelating agents are selected from the group of β-alanine diacetic acid, cyclodextrin, diethylenetriamine penta(methylene phosphonic acid), sodium, potassium, calcium disodium, ammonium, and triethanolamine salts of ethylenediamine tetraacetic acid (EDTA), etidronic acid, hydroxyethyl ethylenediamine tetraacetic acid (HEDTA) and sodium salts thereof, sodium salts of nitrilotriacetic acid (NTA), diethylenetriamine pentaacetic acid, phytic acid, hydroxypropyl cyclodextrin, methyl cyclodextrin, pentasodium amino trimethylene phosphonate, pentasodium ethylenediamine tetramethylene phosphonate, pentasodium diethylenetriaminepentaacetate, pentasodium triphosphate, potassium EDTMP, sodium EDTMP, sodium dihydroxyethylglycinate, sodium phytate, sodium polydimethylglycinophenol sulfonate, tetrahydroxyethyl ethylenediamine, tetrahydroxypropyl ethylenediamine, tetrapotassium etidronate, tetrasodium etidronate, tetrasodium iminodisuccinate, trisodium ethylenediamine disuccinate, tetrasodium N,N-bis(carboxymethyl)-glutamate, tetrasodium DL-alanine-N,N-diacetate, and desferrioxamine.

The deodorizing action of the antiperspirant cosmetic agents according to the invention can be increased further if at least one deodorant active substance having antibacterial and/or bacteriostatic and/or enzyme-inhibiting and/or odor-neutralizing and/or odor-absorbing action is additionally included in a total amount of 0.0001 to 40 wt %, preferably 0.2 to 20 wt %, more preferably 1 to 15 wt %, particularly 1.5 to 5 wt %, with respect to the total weight of the propellant-free antiperspirant cosmetic agent according to the invention. If ethanol is used in the agents according to the invention, the ethanol is not considered to be a deodorant active substance in the context of the present invention, but rather a constituent of the carrier. Deodorant active substances preferred according to the invention are disclosed, for example, in laid-open application DE 102010063250 A1.

Preferred antiperspirant cosmetic agents according to the invention also include at least one water-soluble polyhydric $C_{2-9}$ alkanol having 2 to 6 hydroxyl groups and/or at least one water-soluble polyethylene glycol having 3 to 50 ethylene oxide units and mixtures thereof. The aforementioned deodorant active substances in the form of 1,2-alkanediols do not fall thereunder. Preferred alkanols and water-soluble polyethylene glycols are described, for example, in laid-open application DE 102010063250 A1.

According to another embodiment of the present invention, the antiperspirant cosmetic agents also include at least one skin-cooling active substance. Skin-cooling active substances suitable according to the invention are, for example, menthol, isopulegol, and menthol derivatives, e.g., menthyl lactate, menthyl glycolate, menthyl ethyl oxamate, menthyl pyrrolidone carboxylic acid, menthyl methyl ether, menthoxypropanediol, menthone glycerin acetal (9-methyl-6-(1-methylethyl)-1,4-dioxaspiro[4.5]decane-2-methanol), monomenthyl succinate, 2-hydroxymethyl-3,5,5-trimethylcyclohexanol, and 5-methyl-2-(1-methylethyl)cyclohexyl-N-ethyloxamate. Menthol, isopulegol, menthyl lactate, menthoxypropanediol, menthyl pyrrolidone carboxylic acid, and 5-methyl-2-(1-methylethyl)cyclohexyl-N-ethyloxamate and mixtures of these substances, particularly mixtures of menthol and menthyl lactate, menthol, menthol glycolate, and menthyl lactate, menthol and menthoxypropanediol, or menthol and isopulegol, are preferred as skin-cooling active substances.

According to the invention, preferably acids and/or alkalizing agents and/or buffers are used as pH adjusters. According to the invention, preferably inorganic acids (such as hydrochloric acid, sulfuric acid, or phosphoric acid) or organic acids (such as citric acid, gluconic acid, tartaric acid, or malic acid) are used as acids. The alkalizing agents that are usable according to the invention are preferably selected from the group consisting of ammonia, basic amino acids, alkali hydroxides, carbonates and hydrogencarbonates, alkanolamines, such as amino-2-methyl-1-propanol, monoethanolamine, triethanolamine, diethanolamine, and triisopropanolamine, alkali metal metasilicates, urea, morpholine, N-methylglucamine, imidazole, alkali phosphates, and alkali hydrogenphosphates. Preferably lithium, sodium, potassium, particularly sodium or potassium, is used as an alkali metal ion. In particular, carbonic acid/bicarbonate buffer, carbonic acid/silicate buffer, acetic acid/acetate buffer, phosphate buffer, ammonia buffer, citric acid or citrate buffer, buffer based on tris(hydroxymethyl)aminomethane, buffer based on 4-(2-hydroxyethyl)-1-piperazineethanesulfonic acid, buffer based on 4-(2-hydroxyethyl)piperazine-1-propanesulfonic acid, buffer based on 2-(N-morpholino)ethanesulfonic acid, and barbital/acetate buffer are suitable as buffer systems in the context of the present invention. The appropriate buffer system is selected in accordance with the desired pH value of the antiperspirant cosmetic agents according to the invention.

In a preferred embodiment, the antiperspirant cosmetic agents according to the invention are characterized in that said agents include—with respect to the total weight of the propellant-free antiperspirant cosmetic agent
- at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %,
- 12 to 98 wt %, preferably 25 to 55 wt %, more preferably 30 to 50 wt %, particularly 35 to 45 wt %, of water,
- at least one emulsifier and/or one surfactant,
- at least one pH adjuster,
- at least one preservative agent, and
- at least one substance selected from the group of cosmetic oils that are liquid at 20° C. and 1,013 hPa, odorous substances, and waxes.

In another preferred embodiment, the antiperspirant cosmetic agents according to the invention are characterized in that said agents include—with respect to the total weight of the propellant-free antiperspirant cosmetic agent according to the invention
- at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %,
- 12 to 98 wt %, preferably 25 to 55 wt %, more preferably 30 to 50 wt %, particularly 35 to 45 wt %, of water,
- at least one emulsifier and/or one surfactant,
- at least one pH adjuster,
- at least one preservative agent,
- 0.01 to 5 wt %, preferably 0.1 to 2 wt %, more preferably 0.2 to 0.7 wt %, particularly 0.3 to 0.5 wt %, of a thickener, and
- at least one substance selected from the group of cosmetic oils that are liquid at 20° C. and 1,013 hPa, odorous substances, and waxes.

In a preferred embodiment, the antiperspirant cosmetic agents according to the invention are characterized in that said agents include—with respect to the total weight of the propellant-free antiperspirant cosmetic agent according to the invention
- at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %,
- 12 to 98 wt %, preferably 25 to 55 wt %, more preferably 30 to 50 wt %, particularly 35 to 45 wt %, of water,
- at least one propellant in a total amount of 1 to 98 wt %, preferably 20 to 90 wt %, more preferably 30 to 85 wt %, particularly 40 to 75 wt %,
- at least one emulsifier and/or one surfactant,
- at least one pH adjuster,
- at least one preservative agent, and at least one substance selected from the group of cosmetic oils that are liquid at 20° C. and 1,013 hPa, odorous substances, and waxes.

In another preferred embodiment, the antiperspirant cosmetic agents according to the invention are characterized in that said agents include—with respect to the total weight of the propellant-free antiperspirant cosmetic agent according to the invention
- at least one chitosan of formula (I) in a total amount of 0.05 to 40 wt %, preferably 0.1 to 35 wt %, more preferably 0.2 to 30 wt %, even more preferably 0.4 to 25 wt %, particularly 0.5 to 20 wt %,
- 12 to 98 wt %, preferably 25 to 55 wt %, more preferably 30 to 50 wt %, particularly 35 to 45 wt %, of water,
- at least one propellant in a total amount of 1 to 98 wt %, preferably 20 to 90 wt %, more preferably 30 to 85 wt %, particularly 40 to 75 wt %,
- at least one emulsifier and/or one surfactant,
- at least one pH adjuster,
- at least one preservative agent,
- 0.01 to 5 wt %, preferably 0.1 to 2 wt %, more preferably 0.2 to 0.7 wt %, particularly 0.3 to 0.5 wt %, of a thickener, and
- at least one substance selected from the group of cosmetic oils that are liquid at 20° C. and 1,013 hPa, odorous substances, and waxes.

In the context of the present invention, it can also be provided that the cosmetic agent according to the invention is formulated as a two-component agent. For this purpose, the individual components are preferably stored in separate containers and are applied to the skin one after the other in any order or simultaneously. Separation into multi-component systems is preferred particularly if incompatibility of the ingredients is expected or feared.

Therefore, another subject of the present invention is a packaging unit (kit of parts), comprising—produced separate from each other
a) at least one first container (C1), containing a cosmetic agent (M1) comprising at least one antiperspirant active substance, and
b) at least one second container (C2), containing a cosmetic agent (M2) comprising at least one chitosan of formula (I),

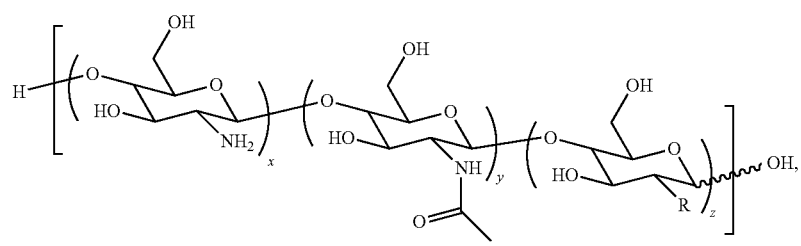

wherein
x and z, independently of each other, represent integers from 5 to 25,000,
y represents integers from 1 to 25,000,
R represents an $NH_2$ group or $*-NH_3^+CH_3CH(OH)C(O)O^-$ or $*-NH_3^+OHCH_2C(O)O^-$,
with the stipulation that the sequence of the units included in the square brackets and having the indices x, y, and z can be freely chosen and the residue R is bonded by means of *, and wherein the cosmetic agent (M2) includes no aluminum-containing compounds.

According to the invention, the term "antiperspirant active substance" is understood to mean active substances that reduce the perspiration of the sweat glands of the body. However, the chitosans of formula (I) that are included in the cosmetic agent (M2) do not fall thereunder.

The statements made with respect to the cosmetic agents according to the invention apply, mutatis mutandis, to other embodiments of the packaging unit according to the invention.

Another subject of the present invention is the use of at least one chitosan to at least partially influence the sweat gland(s), wherein the chitosan has the formula (I),

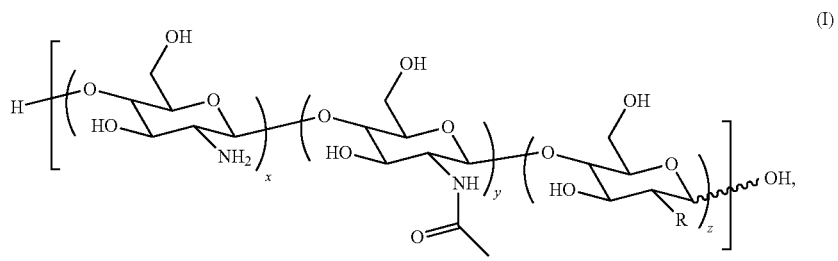

(I)

wherein x and z, independently of each other, represent integers from 5 to 25,000, y represents integers from 1 to 25,000, R represents an $NH_2$ group or $*-NH_3^+CH_3CH(OH)C(O)O^-$ or $*-NH_3^+OHCH_2C(O)O^-$, with the stipulation that the sequence of the units included in the square brackets and having the indices x, y, and z can be freely chosen and the residue R is bonded by means of *.

According to the invention, "to influence the sweat gland(s)" and "influence on the sweat gland(s)" should be understood to mean the influencing of the sweat gland(s) in such a way that the secretion of sweat from the excretory duct is avoided or reduced. With no intention of being restricted to one theory, this can be accomplished by the formation of a precipitate of the at least one specific chitosan of formula (I) in the excretory duct of the sweat gland or the excretory ducts of the sweat glands. However, this can also be accomplished by disturbing the charge equilibrium within the excretory ducts of the sweat glands.

The statements made with respect to the antiperspirant cosmetic agents according to the invention apply, mutatis mutandis, to other embodiments of the use according to the invention.

Furthermore, another subject of the present invention is the use of a combination, including a) at least one substance selected from the group of cosmetic oils that are liquid at 20° C. and 1,013 hPa, odorous substances, and waxes, b) propellant in a total amount of 0 to 99 wt %, with respect to the total weight of the antiperspirant cosmetic agent, and c) at least one chitosan having a viscosity of 15 to 15,000 mPa*s, wherein the chitosan has the formula (I),

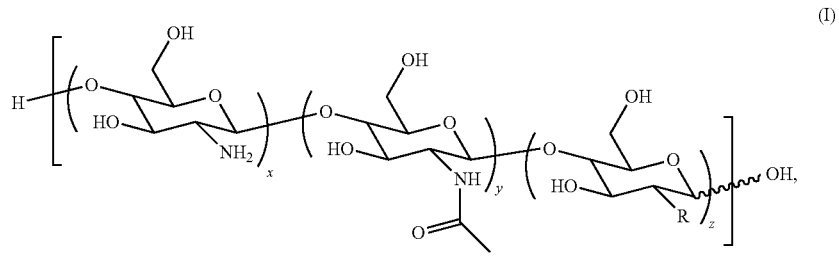

(I)

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units included in the square brackets and having the indices x, y, and z can be freely chosen and the residue R is bonded by means of *, and d) no aluminum-containing compounds, to reduce and/or prevent perspiration, particularly underarm perspiration or perspiration of other body regions.

In the sense of the present invention, the term "combination" comprises a mixture of the ingredients a), b), and c) that are specified above. The statements made with respect to the antiperspirant cosmetic agents according to the invention and to the use according to the invention apply, mutatis mutandis, to other preferred embodiments of the use of the aforementioned combination.

Finally, another subject of the present invention is a non-therapeutic cosmetic method for preventing and/or reducing the perspiration of the body, wherein an antiperspirant cosmetic agent according to the invention or the cosmetic agents (M1) and (M2) of the packaging unit according to the invention are applied to the skin, particularly to the skin of the axillae, and remain on the skin of the axillae for at least 1 hour, preferably for at least 2 hours, more preferably for at least 4 hours, particularly for at least 6 hours.

In the case of the packaging unit according to the invention, it can be provided that first the cosmetic agent (M1) having the antiperspirant active substance is applied and then the cosmetic agent (M2) including at least one chitosan of formula (I) is applied. But it is also possible that first the cosmetic agent (M2) is applied and then a cosmetic agent (M1) is used. Furthermore, the cosmetic agent (M2) and the cosmetic agent (M1) can also be applied to the skin simultaneously. The time span between the application of said two agents is 0 seconds to 24 hours.

Furthermore, in the context of this subject of the invention, it is preferred if the cosmetic agent or the cosmetic agents remain on the skin of the axillae for at least 1 hour, preferably for at least 2 hours, more preferably for at least 4 hours, particularly for at least 6 hours, after the application.

The statements made with respect to the antiperspirant cosmetic agents according to the invention and to the use according to the invention apply, mutatis mutandis, to other preferred embodiments of the method according to the invention.

The present invention is outlined particularly by means of the following points:

An antiperspirant cosmetic agent, including a) at least one substance selected from the group of cosmetic oils that are liquid at 20° C. and 1,013 hPa, odorous substances, and waxes, b) propellant in a total amount of 0 to 99 wt %, with respect to the total weight of the antiperspirant cosmetic agent, and c) at least one chitosan having a viscosity of 15 to 15,000 mPa*s, wherein the chitosan has the formula (I),

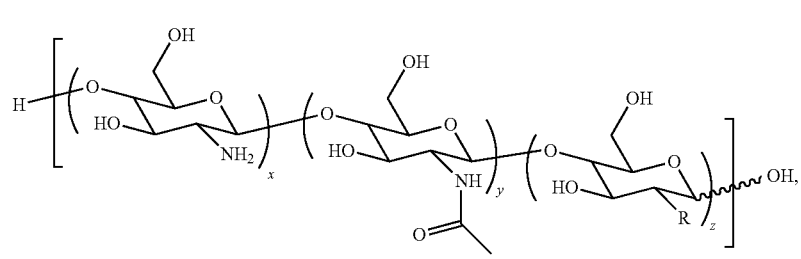

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units included in the square brackets and having the indices x, y, and z can be freely chosen and the residue R is bonded by means of *, and d) no aluminum-containing compounds.

The antiperspirant cosmetic agent according to point 1, characterized in that the viscosity is determined by means of a Brookfield RVDV II+, spindle no. 2, at 20 rpm and at 20° C., by using 1 wt % of chitosan of formula (I) in a 1 wt % acetic acid solution, with respect to the total weight of the solution.

The antiperspirant cosmetic agent according to one of points 1 and 2, characterized in that y represents integers from 1 to 22,000, preferably from 1 to 20,000, more preferably from 1 to 19,000, even more preferably from 1 to 18,000, particularly from 1 to 17,500, in formula (I).

The antiperspirant cosmetic agent according to one of the preceding points, characterized in that x and z, independently of each other, represent integers from 5 to 20,000, preferably from 6 to 15,200, more preferably from 7 to 13,000, even more preferably from 8 to 12,500, particularly from 10 to 11,700, in formula (I).

The antiperspirant cosmetic agent according to one of the preceding points, characterized in that the at least one chitosan of formula (I) has a degree of deacetylation of 70 to 99%, preferably 80 to 98%, more preferably 80 to 95%, even more preferably 80 to 92%, particularly 80 to 90%.

The antiperspirant cosmetic agent according to one of the preceding points, characterized in that the at least one chitosan of formula (I) is isolated from marine sources, particularly crabs, shrimps, krill, fungi, zooplankton, insects, microorganisms, modified microorganisms, or plant sources.

The antiperspirant cosmetic agent according to one of the preceding points, characterized in that the at least one chitosan of formula (I) has an average molecular weight $M_w$ of 5,000 to 6,000,000 Da, preferably 6,000 to 5,500,000 Da, more preferably 8,000 to 5,050,000 Da, particularly 10,000 to 5,000,000 Da.

The antiperspirant cosmetic agent according to one of the preceding points, characterized in that the at least one chitosan of formula (I) has a viscosity of 15 to 10,000 mPa*s, preferably 15 to 8,000 mPa*s, more preferably 15 to 6,000 mPa*s, particularly 15 to 5,000 mPa*s, wherein the viscosity is determined by means of a Brookfield RVDV II+, spindle no. 2, at 20 rpm and at 20° C., and wherein 1 wt % of chitosan of formula (I) in a 1 wt % acetic acid solution, with respect to the total weight of the solution, is used to determine the viscosity.

The antiperspirant cosmetic agent according to one of the preceding points, characterized in that the at least one chitosan of formula (I) is included in a total amount of 0.05 to 40 wt %, preferably 0.1 to 35 wt %, more preferably 0.2 to 30 wt %, even more preferably 0.4 to 25 wt %, particularly 0.5 to 20 wt %, with respect to the total weight of the propellant-free antiperspirant cosmetic agent.

The antiperspirant cosmetic agent according to one of the preceding claims, characterized in that the antiperspirant cosmetic agent has a pH value of pH 2 to pH 6.

A packaging unit (kit of parts), comprising—produced separate from each other
a) at least one first container (C1), containing a cosmetic agent (M1) comprising at least one antiperspirant active substance, and
b) at least one second container (C2), containing a cosmetic agent (M2) comprising at least one chitosan of formula (I),

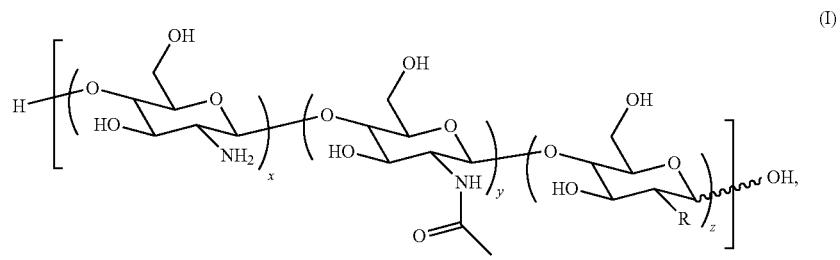

(I)

wherein
x and z, independently of each other, represent integers from 5 to 25,000,
y represents integers from 1 to 25,000,
R represents an $NH_2$ group or *—$NH_3^+CH_3CH(OH)C(O)O^-$ or *—$NH_3^+OHCH_2C(O)O^-$,
with the stipulation that the sequence of the units included in the square brackets and having the indices x, y, and z can be freely chosen and the residue R is bonded by means of *, and wherein the cosmetic agent (M2) includes no aluminum-containing compounds.

The use of at least one chitosan to at least partially influence the sweat gland(s), wherein the chitosan has the formula (I),

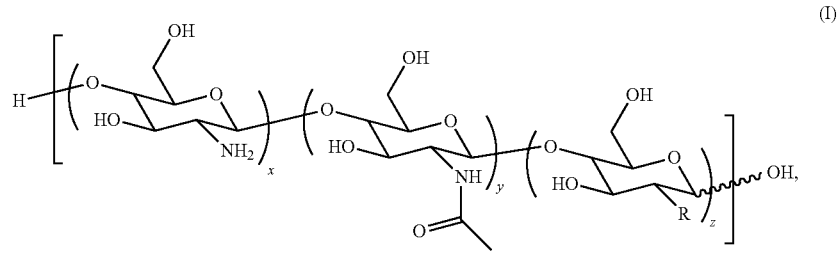

(I)

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units included in the square brackets and having the indices x, y, and z can be freely chosen and the residue R is bonded by means of *.

The use of a combination, including a) at least one substance selected from the group of cosmetic oils that are liquid at 20° C. and 1,013 hPa, odorous substances, and waxes, b) propellant in a total amount of 0 to 99 wt %, with respect to the total weight of the antiperspirant cosmetic agent, and c) at least one chitosan having a viscosity of 15 to 15,000 mPa*s, wherein the chitosan has the formula (I),

TABLE 1

| Sample solution (specifications in wt %) | | |
|---|---|---|
| | E-I* | E-II* |
| Chitosan 1 a) | 0.25 | — |
| Chitosan 2 b) | — | 0.10 |
| Lactic acid | 0.07 | 0.18 |
| HCl | ad pH | ad pH |
| Water | ad 100 | ad 100 |

*according to the invention a) R = *—$NH_3^+CH_3CH(OH)C(O)O^-$, $M_w$ = 50,000 to 1,000,000 Da, viscosity = 70 to 150 mPa*s, degree of deacetylation ≥ 80%, marine source b) R = *—$NH_3^+CH_3CH(OH)C(O)O^-$, $M_w$ = 10,000 to 20,000 Da, viscosity = 20 to 40 mPa*s, degree of deacetylation ≥ 80%, plant source For the determination of the opacification, a Methrom Titrando 905 from the company Methrom (USA) was used, which is equipped with a Methrom Optrode 6.1115.000 and a pH electrode from Methrom. The Methrom Titrando 905

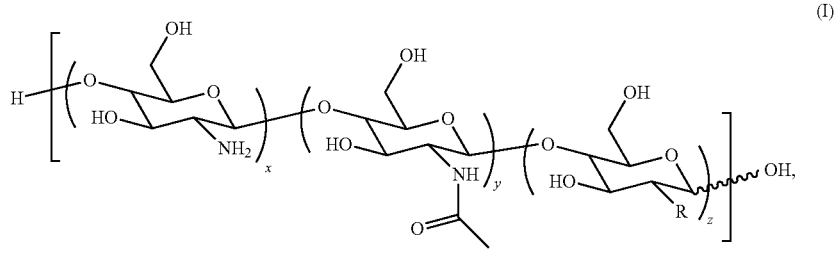

(I)

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units included in the square brackets and having the indices x, y, and z can be freely chosen and the residue R is bonded by means of *, and d) no aluminum-containing compounds, to reduce and/or prevent perspiration, particularly underarm perspiration or perspiration of other body regions.

A non-therapeutic cosmetic method for preventing and/or reducing the perspiration of the body, wherein an antiperspirant cosmetic agent according to one of points 1 to 10 or the cosmetic agents (M1) and (M2) of the packaging unit according to point 11 are applied to the skin, particularly to the skin of the axillae, and remain on the skin of the axillae for at least 1 hour, preferably for at least 2 hours, more preferably for at least 4 hours, particularly for at least 6 hours.

The following examples illustrate the present invention without restricting the present invention to said examples:

EXAMPLES

1. Determination of the Opacification

The determination of the opacification that is caused by the following chitosans in a pH range of 5.5 to 7.5 in the event of a pH value change of 0.5 is performed as follows:

is controlled by means of the Tiamo software from Methrom. First, 30 ml of a sample solution according to table 1, which had a pH value of 3.0, was provided in the open sample vessel of the Methrom Titrando 905. Then, at 23° C. and 1,013 mbar and while stirring (stirring speed 8 of the Titrando 905), a 1 wt % sodium hydrogen carbonate solution was added continuously until a pH value of 7.5 was reached. During the addition of the 1 wt % sodium hydrogen carbonate solution, the light transmission of a light beam through said sample solution was measured in mV (resolution of 0.1 mV) at a wavelength of 574 nm (greenish yellow) by using a Methrom Optrode 6.1115.000. Each measurement is performed twice and the mean is calculated therefrom.

The opacification, or change in the light absorption, that was caused by the aforementioned chitosans was determined in accordance with the formula $\Delta L=[(|L_i|/|L_0|)]*100$. In this formula, $L_i$ represents the difference of the light transmission before and after a change in the pH value by at least 0.5 in the pH range of 4.0 to 8.0, preferably pH 4.5 and 7.5, particularly pH 5.0 and 7.0. In this formula, $L_0$ represents the difference of the light transmission at pH 4.0 and at pH 8.0, preferably at pH 4.5 and at pH 7.5, particularly at pH 5.0 and at pH 7.0.

In the event of a pH value change of 0.5 between pH 6.0 and pH 6.5 (difference of light absorption at pH 6.5 minus light absorption at pH 6.0 forms the value $L_i$) in a pH value range of 5.5 to 7.5 (difference of light absorption at pH 7.5 minus light absorption at pH 5.5 forms the value $L_0$), said chitosans caused the change in the light absorption $\Delta L$, or opacification, indicated in table 2.

TABLE 2

| Change in the light absorption ΔL, or opacification | |
|---|---|
| Sample solution | ΔL [%] |
| E-I (chitosan 1) | 30 |
| E-II (chitosan 2) | 4 |

2. Formulations:

The following chitosans of formula (I) are preferably used in the examples below:

R=*—$NH_3^+CH_3CH(OH)C(O)O^-$, $M_w$=50,000 to 1,000,000 Da, viscosity=70 to 150 mPa*s, degree of deacetylation≥80%, marine source R=*—$NH_3^+CH_3CH(OH)C(O)O^-$, $M_w$=50,000 to 1,000,000 Da, viscosity=1,000 to 5,000 mPa*s, degree of deacetylation≥80%, marine source R=*—$NH_3^+OHCH_2C(O)O^-$, $M_w$=500,000 to 5,000,000 Da, viscosity=500 to 5,000 mPa*s, degree of deacetylation≥80%, marine source R=$NH_2$ group, $M_w$=300,000 to 2,000,000 Da, viscosity=150 to 1,000 mPa*s, degree of deacetylation≥80%, marine source R=$NH_2$ group, $M_w$=50,000 to 5,000,000 Da, viscosity=1,850 to 2,250 mPa*s, degree of deacetylation≥80%, marine source R=*—$NH_3^+CH_3CH(OH)C(O)O^-$, $M_w$=10,000 to 20,000 Da, viscosity=20 to 40 mPa*s, degree of deacetylation≥80%, plant source Antiperspirant cosmetic agents according to the invention having a pH of 2.5 to 6.0 (amount specifications in wt %)

| | 1 | 2 | 3 | 4 | 5 | 6 | 7 |
|---|---|---|---|---|---|---|---|
| Isopropyl myristate | 0.50 | 0.10 | 0.50 | 1.0 | 2.0 | 3.0 | 5.0 |
| Chitosan of formula (I) | 0.05 | 0.1 | 0.2 | 0.3 | 0.4 | 1.5 | 2.0 |
| Eumulgin B3 [a] | 3.0 | 3.0 | 3.0 | 4.0 | 4.0 | 4.0 | 5.0 |
| Perfume | 0.10 | 0.20 | 0.30 | 0.30 | 0.30 | 0.30 | 0.30 |
| Preservative agent | 0.50 | 0.50 | 0.50 | 0.80 | 0.80 | 1.5 | 2.0 |
| pH adjuster | ad pH | ad pH | ad pH | ad pH | ad pH | ad pH | ad pH |
| Water | ad 100 | ad 100 | ad 100 | ad 100 | ad 100 | ad 100 | ad 100 |

[a] Eumulgin B3 (INCI: Ceteareth-30; BASF)

Antiperspirant cosmetic agents according to the invention having a pH of 2.5 to 6.0, in the form of sprayable emulsions (amount specifications in wt %)

| | 1 | 2 | 3 | 4 |
|---|---|---|---|---|
| Cyclopentasiloxane | 11 | 11 | 13 | 15 |
| Isopropyl myristate | 5.0 | 5.0 | 5.0 | 5.0 |
| Dow Corning ES-5227 DM [b] | 6.0 | 6.0 | 7.0 | 7.0 |
| Perfume | 4.0 | 4.0 | 5.0 | 4.0 |
| Propylene glycol | 20 | 20.5 | 18 | 15 |
| Phenoxyethanol | 0.5 | 0.5 | 0.5 | 0.5 |
| Sodium benzoate | 0.4 | 0.4 | 0.4 | 0.4 |
| Chitosan of formula (I) | 1.0 | 0.5 | 2.0 | 0.5 |
| Hydrochloric acid, 20% | ad pH | ad pH | ad pH | ad pH |
| Water | ad 100 | ad 100 | ad 100 | ad 100 |

[b] Dow Corning ES-5227 (INCI: Dimethicone, PEG/PPG-18/18 Dimethicone; Dow Corning)

Antiperspirant cosmetic agents according to the invention having a pH of 2.5 to 6.0, in the form of roll-ons (amount specifications in wt %)

| | 1 | 2 | 3 | 4 |
|---|---|---|---|---|
| Steareth-21 | 1.5 | 1.5 | 2.0 | 2.0 |
| Steareth-2 | 2.5 | 2.5 | 3.0 | 2.0 |
| PPG-15 stearyl ether | 0.5 | 0.5 | 1.0 | 0.5 |
| Perfume | 1.0 | 1.0 | 1.5 | 1.0 |
| Tetrasodium EDTA | 0.1 | 0.1 | 0.1 | 0.1 |
| Chitosan of formula (I) | 1.0 | 0.5 | 2.0 | 0.5 |
| Hydrochloric acid, 20% | ad pH | ad pH | ad pH | ad pH |
| Water | ad 100 | ad 100 | ad 100 | ad 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for preventing and/or reducing the perspiration of the body, comprising applying an antiperspirant cosmetic agent to a skin of the axillae and leaving the cosmetic agent on the skin for at least 1 hour, wherein the antiperspirant cosmetic agent comprises a) at least one substance selected from the group consisting of: cosmetic oils that are liquid at 20° C. and 1,013 hPa, odorous substances, and waxes, b) propellant in a total amount of 1 to 99 wt %, with respect to the total weight of the antiperspirant cosmetic agent, and c) at least one chitosan having a viscosity of 20 to 40 mPa*s, wherein the chitosan has the formula (I),

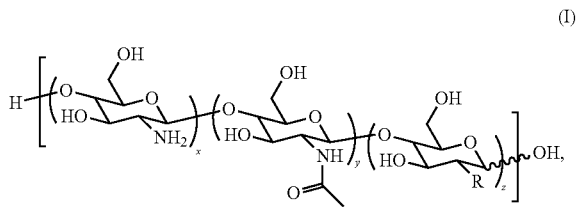

wherein x and z, independently of each other, represent integers from 5 to 25,000, y represents integers from 1 to 25,000, R represents an $NH_2$ group or *—$NH_3^+CH_3CH(OH)C(O)O^-$ or *—$NH_3^+OHCH_2C(O)O^-$, with the stipulation that the sequence of the units contained in the square brackets and having the indices x, y, and z can be freely chosen and the residue R is bonded by means of *, and d) no aluminum-containing compounds, and e) 30 to 70 wt % free water, with respect to the total weight of the propellant-free antiperspirant cosmetic agent.

2. The method for preventing and/or reducing the perspiration of the body according to claim 1, wherein y represents integers from 1 to 22,000 in formula (I).

3. The method for preventing and/or reducing the perspiration of the body according to claim 1, wherein y represents integers, from 1 to 17,500, in formula (I).

4. The method for preventing and/or reducing the perspiration of the body according to claim 1, wherein x and z, independently of each other, represent integers from 5 to 20,000 in formula (I).

5. The method for preventing and/or reducing the perspiration of the body according to claim 1, wherein x and z, independently of each other, represent integers from 10 to 11,700, in formula (I).

6. The method for preventing and/or reducing the perspiration of the body according to claim 1, wherein the at least one chitosan of formula (I) has a degree of deacetylation of 70 to 99%.

7. The method for preventing and/or reducing the perspiration of the body according to claim 1, wherein the at least one chitosan of formula (I) has a degree of deacetylation of 80 to 90%.

8. The method for preventing and/or reducing the perspiration of the body according to claim 1, wherein the at least one chitosan of formula (I) is included in a total amount of 0.05 to 40 wt % with respect to the total weight of the propellant-free antiperspirant cosmetic agent.

9. The method for preventing and/or reducing the perspiration of the body according to claim 1, wherein the at least one chitosan of formula (I) is included in a total amount of 0.5 to 20 wt % with respect to the total weight of the propellant-free antiperspirant cosmetic agent.

10. The method for preventing and/or reducing the perspiration of the body according to claim 1, wherein the at least one chitosan of formula (I) is included in a total amount of 0.2 to 30 wt % with respect to the total weight of the propellant-free antiperspirant cosmetic agent.

* * * * *